(12) United States Patent
Winer

(10) Patent No.: US 10,595,652 B1
(45) Date of Patent: Mar. 24, 2020

(54) PILLOW CUSTOMIZATION SYSTEM AND METHOD

(71) Applicant: Richard Winer, Austin, TX (US)

(72) Inventor: Richard Winer, Austin, TX (US)

(73) Assignee: RDUB Consulting, Inc, Austin ( * ) Notice: Subject to any disclaimer, the term of this patent is extended or adjusted under 35 U.S.C. 154(b) by 0 days.

(21) Appl. No.: 16/549,364

(22) Filed: Aug. 23, 2019

Related U.S. Application Data

(63) Continuation-in-part of application No. 16/211,858, filed on Dec. 6, 2018.

(60) Provisional application No. 62/760,593, filed on Nov. 13, 2018.

(51) Int. Cl.
*A47G 9/10* (2006.01)
*G06K 9/00* (2006.01)
*G06Q 30/06* (2012.01)

(52) U.S. Cl.
CPC .......... *A47G 9/10* (2013.01); *G06K 9/00369* (2013.01); *G06Q 30/0621* (2013.01); *A47G 2009/1018* (2013.01)

(58) Field of Classification Search
CPC ................. G06K 9/00369; G06Q 30/0621
See application file for complete search history.

(56) References Cited

U.S. PATENT DOCUMENTS

| | | | |
|---|---|---|---|
| 2017/0202366 A1* | 7/2017 | Mackey | A47C 31/123 |
| 2018/0027988 A1* | 2/2018 | Poodeh | A47C 31/123 |

* cited by examiner

*Primary Examiner* — Edward Park
(74) *Attorney, Agent, or Firm* — Richard Eldredge

(57) ABSTRACT

A method of pillow customization includes analyzing shapes associated with people through the use of sensors to create analytical data; receiving photos from a subject user through a first computing device and a server; determining a firmness of a mattress of the subject user based on the photos; determining body measurements of the subject based on the photos through one or more algorithms and a second computing device; providing the subject user with a pillow diagram, the pillow diagram having one or more zones, each of the one or more zones being customizable in firmness; receiving one or more subject user inputted selections through the first computing device; and designing a pillow based on the firmness of the mattress, the body measurements, and the one or more subject user inputted characteristics, the pillow being customized to the subject user.

11 Claims, 21 Drawing Sheets

PILLOW CUSTOMIZATION SYSTEM AND METHOD

BACKGROUND

1. Field of the Invention

The present invention relates generally to pillows, and more specifically, to a pillow customization system and method for providing a user with a completely custom pillow that suits their needs, mattress firmness, and body. The system and method of the present invention provides for a customized pillow that will reduce sleeplessness due to crooked necks, unsupported neck discomfort, shoulder and back strain, and overall general user discomfort. The system can further aid in reducing snoring, apnea, and insomnia.

2. Description of Related Art

Pillows are well known in the art and are effective means to provide comfort to a user during rest and sleep. For example, FIG. 1 depicts a conventional pillow 101 having a body 103 on which the user rests their head during use. Pillow 101 has many shortcomings, including general user dissatisfaction.

It should be appreciated that many people suffer from trouble sleeping or staying asleep, one cause of which is an ill-fitting pillow. There are a variety of buying options when it comes to pillows including size, shape, firmness, covering, fillers, and the like. However, these options have conventionally been combined into a few selections for users. Therefore, the user is forced to make an arbitrary selection, likely leading to future discomfort.

In addition, conventional pillow selections are not appropriate for all sleeping positions. People may primarily sleep either on their back, their stomach, or their sides. However, many rotate sleeping positions throughout the night. A perfectly sized pillow will keep a side-sleeping person's head aligned with their spine and will keep a back-sleeping person's head aligned with their spine as well. Since there is generally not a pillow that can accommodate both positions, the person will find a crook in their neck when they wake up or even have difficulty sleeping because of the discomfort.

In addition, pillows ideally need to be matched with a person's bed—the same pillows that suit a person on their bed would not suit that same person if they bought a new bed (with a new firmness) or slept in a different bed. A person buying a pillow online or in a store, even if they test the pillow in the store, cannot know if that pillow will suit them at home and keep their spine in alignment.

Accordingly, although great strides have been made in the area of pillows, many shortcomings remain, and a custom solution is needed.

DESCRIPTION OF THE DRAWINGS

The novel features believed characteristic of the embodiments of the present application are set forth in the appended claims. However, the embodiments themselves, as well as a preferred mode of use, and further objectives and advantages thereof, will best be understood by reference to the following detailed description when read in conjunction with the accompanying drawings, wherein:

Figure 1:
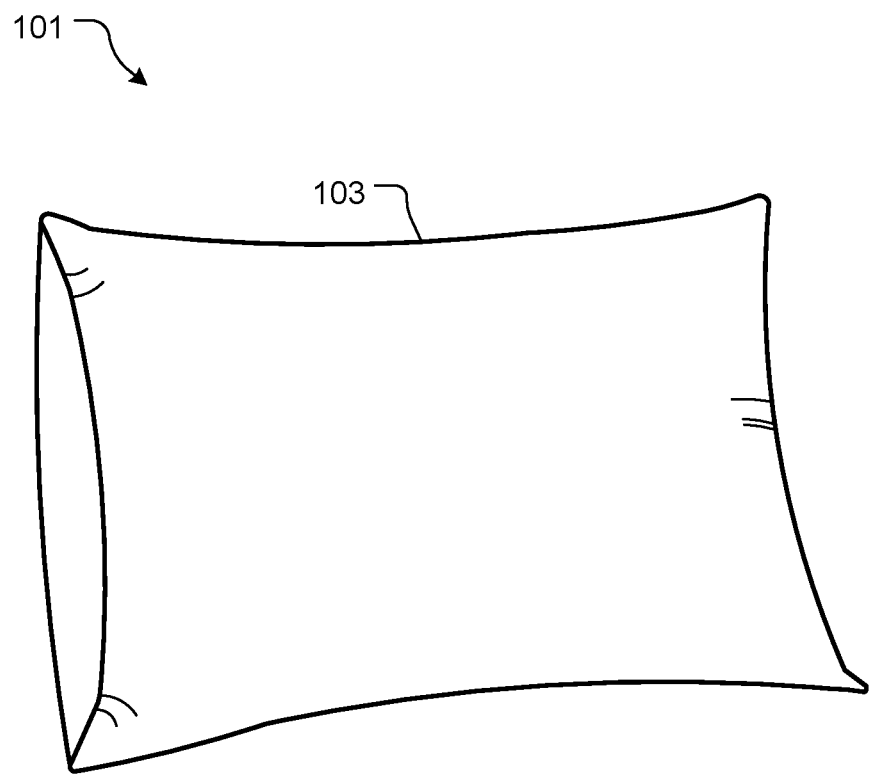
FIG. 1 is an isometric view of a common pillow.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION OF THE PREFERRED EMBODIMENT

Illustrative embodiments of the system and method of use of the present application are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The system and method of use in accordance with the present application overcomes one or more of the above-discussed problems commonly associated with conventional pillows. Specifically, the present invention provides for complete pillow customization based on user photographs and user inputted selections and data. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

The preferred embodiment herein described is not intended to be exhaustive or to limit the invention to the precise form disclosed. It is chosen and described to explain the principles of the invention and its application and practical use to enable others skilled in the art to follow its teachings.

Figure 2:
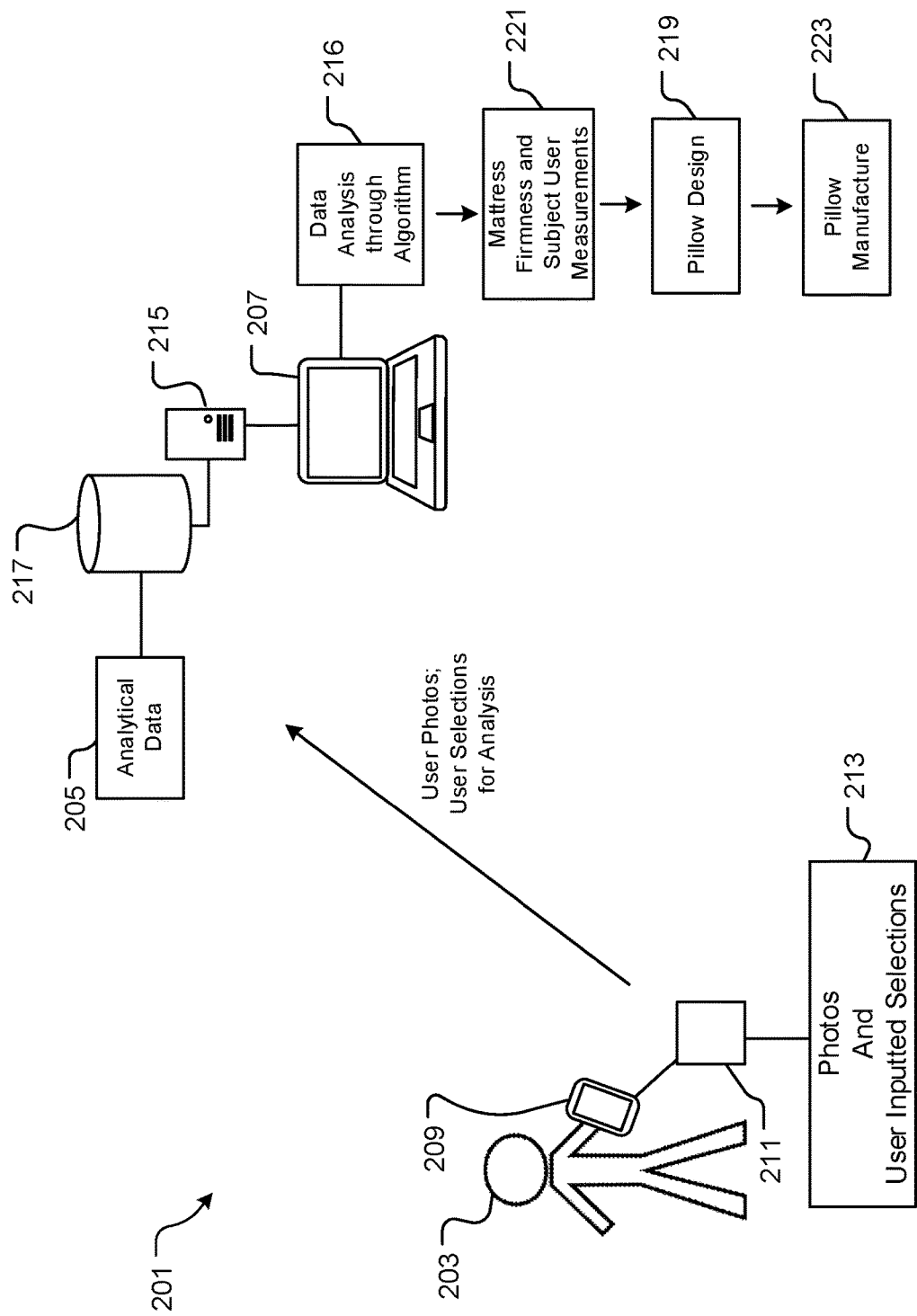
FIG. 2 is a simplified schematic of a pillow customization system in accordance with a preferred embodiment of the present application.

Referring now to the drawings wherein like reference characters identify corresponding or similar elements throughout the several views, FIG. 2 depicts a schematic of a pillow customization system 201 in accordance with a preferred embodiment of the present application. It will be appreciated that system 201 overcomes one or more of the above-listed problems commonly associated with conventional pillows.

In the contemplated embodiment, system 201 includes a subject user 203 for which a customized pillow is to be designed. The system is configured to collect data from the user, process the data, and customize the pillow.

Figure 3:
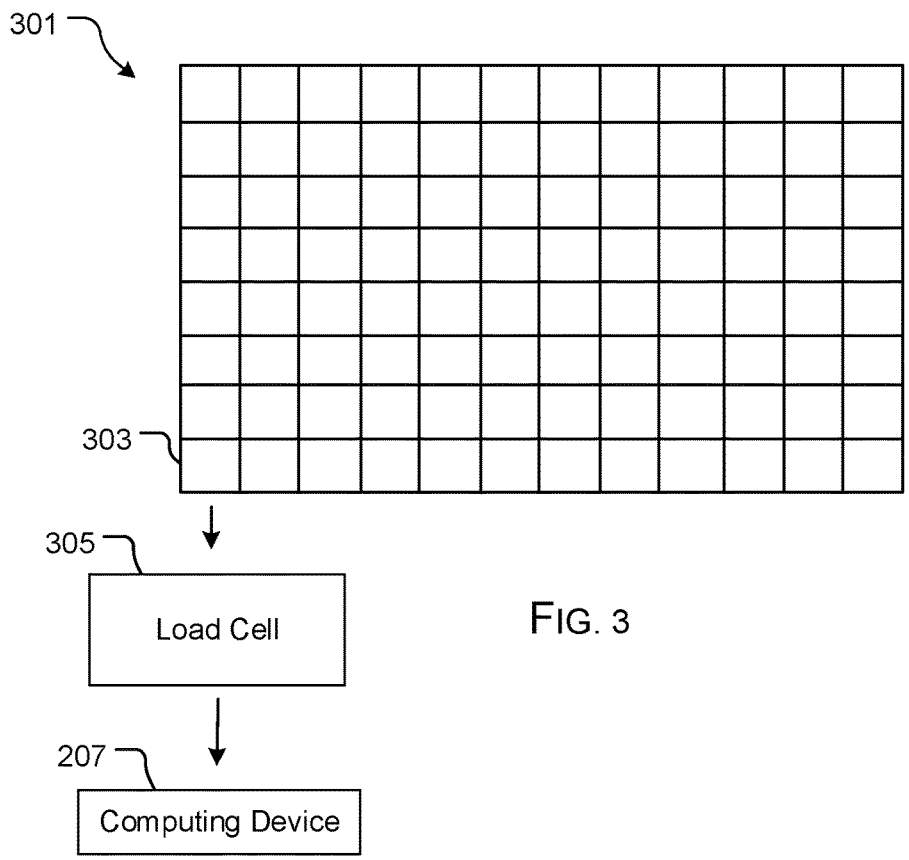
FIG. 3 is a simplified diagram of a data collection and analysis system for collecting data to be used in mattress firmness determination of the system of FIG. 2.

Prior to receiving data from a user, the system is configured to conduct an analysis on the major different kinds of human body shapes, thereby creating analytical data 205, which is used during the data analysis. As shown in FIG. 3, this process is completed through the use of a platform 301 (such as a mattress or the like), wherein a plurality of cells 303 make up the platform, each cell 303 including a sensor 305 configured to communicate with a computing device 207. The plurality of sensors can be any sensor configured to detect a weight of a person lying thereon, including a load cell such as a FlexiForce A502 Sensor.

Figure 4:
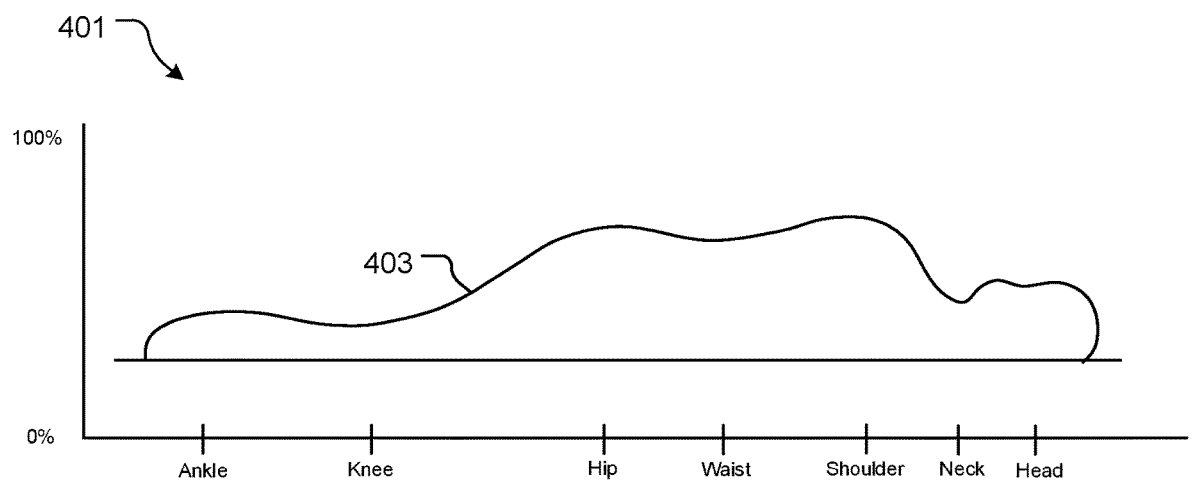
FIG. 4 is a graph of pressure associated with the diagram of FIG. 3.

During use, the plurality of cells 303 collect load data, thereby resulting in a graph 401 as shown in FIG. 4, demonstrating the relative percentage of weight distributed over the height of the person lying thereon by showing the approximate load per section of the body 403. The side sleeper has a lot more weight per square inch than the back sleeper so the force is greater causing the boding to sink more around the shoulders and torso than the back sleeper. This data is used during the analysis, to determine a firmness of the subject user's mattress, which is critical in proper pillow development. As will be discussed herein, using the measurements of a subject user when they are standing (frontal view) and (side view), then comparing it to the photos of them laying on their side and back from the side view, the system is configured to determine the softness of the mattress accurately which will help to calculate the needed factors to properly design a pillow that will custom work for their body shape, body weight and the firmness of their mattress.

Referring back to FIG. 2, the subject user 203 uses a computing device 209 with a platform 211 to upload photos and user selections 213 to a server 215 configured to process data 216 through a database 217 and computing device 207.

Once the photos are taken by the subject user on the computing device, the photos are uploaded to be processed with computing device 207 and associated software and algorithms. The photos are assign a customer number and will be scheduled for manual or automatic digitization to capture the required measurements and adjust them based upon the standard card the user is holding in the photos. After the photos with them laying on their mattress are analyzed the corrected measurements for the pillow will be created. The program will adjust each measurement based upon the size of the credit card, based on the firmness of the mattress, based upon the weight of the individual plus their body type and based upon the compressibility of the selected filler material.

Once the digitization of the measurements are automated, the system is configured to automatically blur out the faces before storing the photos to keep each person's privacy intact. Further, any names/numbers associated with credit cards will further be blurred.

The subject user 203 receives directions on how to take photos through the platform. The computer/server/database are configured to process the photos to determine a mattress firmness and subject user measurements 221. Based on the determined mattress firmness, subject user measurements, and user inputted data, the pillow design 219 is developed and further proceeded to manufacture 223.

To simplify capturing the measurements of a person and the firmness of their bed, having a subject user take several photos of themselves in their home environment solves the problem. A big challenge to overcome when analyzing a photo is the size and dimensions of various objects. One solution is to have people hold a ruler or a tape measure in each photo, however, this may not be convenient for all users. Accordingly, a common object nearly everyone has is a credit card. They are a standard size worldwide of 2⅛ by 3⅛. By having the person hold one during each photo, the relative distances of each measurement can be made. The length and width can be measured and use that to determine the rest of the measurements on each photo. Each customer will be given the choice of several common standard objects such as coins, dollar bills, credit cards, or smart phones to be used as a measurement standard.

The subject user will be provided with sample photos, instructional videos and written instructions as to how to create each required photo. The user will further be shown what the finished photo should look like and provided with a quick checklist to make sure they take the required photos and have followed the instructions for each photo, such as holding the credit card by the corner.

It should be appreciated that one of the unique features believed characteristic of the present application is the use of user provided photos, along with user inputted selections, to develop a fully customizable pillow.

Figure 5A:
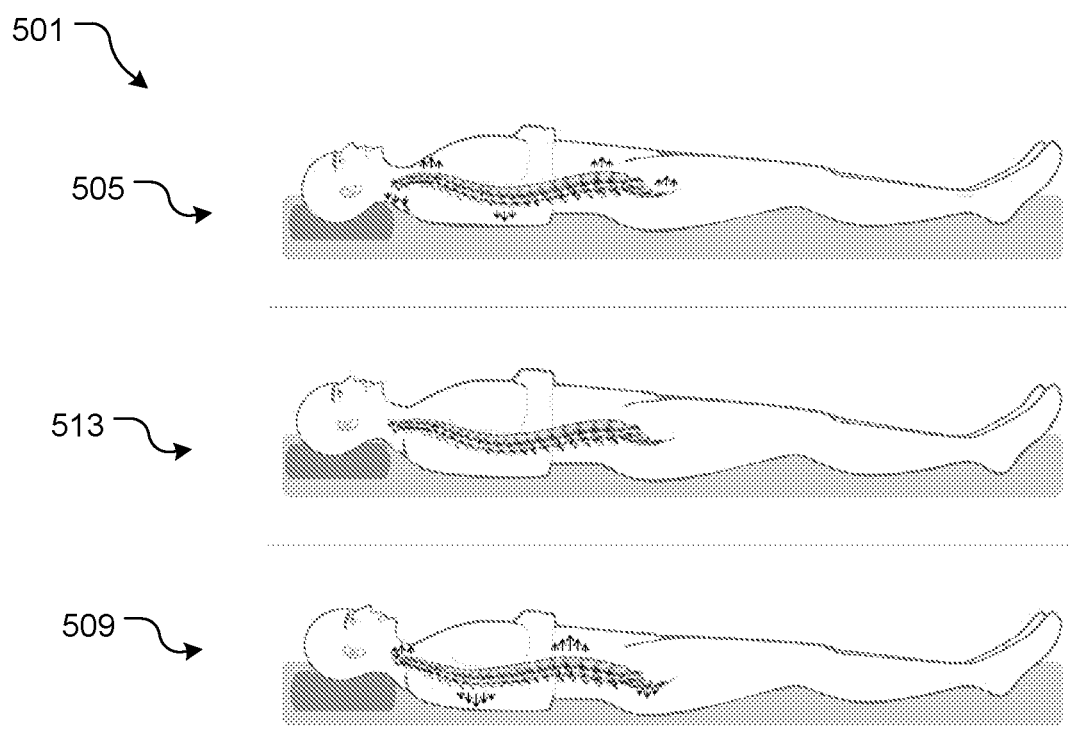
FIGS. 5A and 5B are representative diagrams depicting spine alignment caused by pillows that are too firm, ideal, and too soft.
Figure 5B:
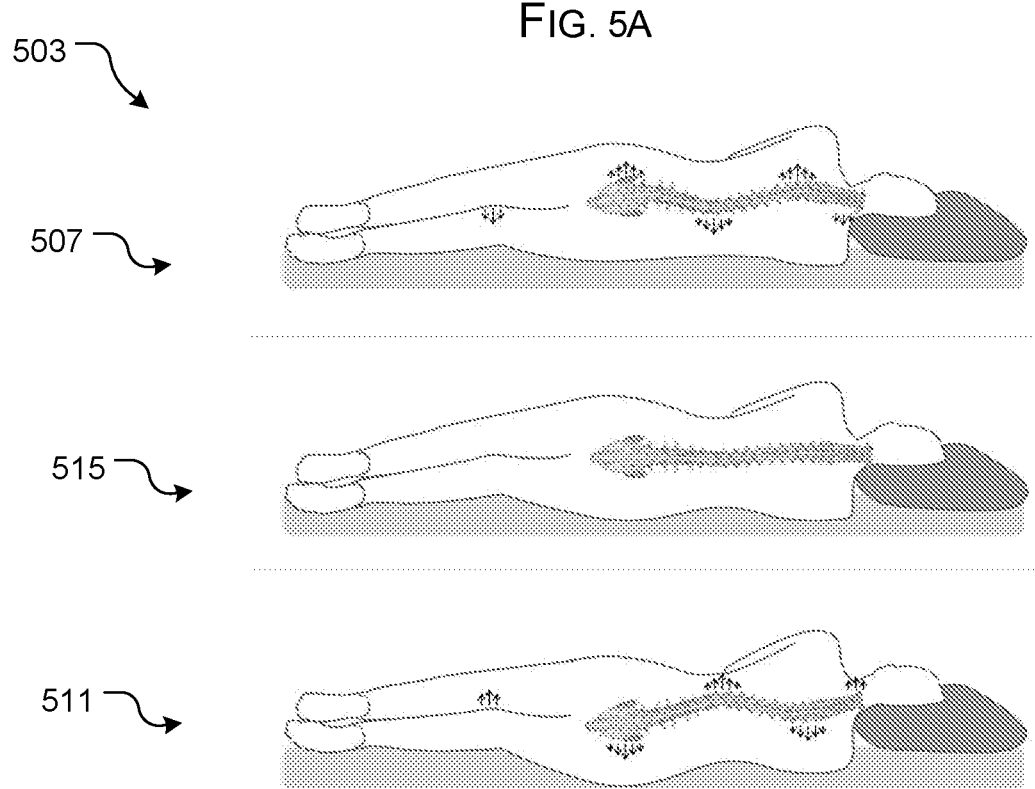

In FIGS. 5A and 5B, diagrams 501, 503 are shown depicting visual representation of spine alignment caused by having a pillow that is too firm 505, 507, too soft 509, 511, and ideal 513, 515. It should be appreciated that the proper pillow firmness based on the user measurements, and the user mattress firmness, provides the user with a pillow that aligns the user spine properly, thereby preventing discomfort.

One of the unique features believed characteristic of the present invention is the ability to calculate the firmness of the subject user's mattress. This is important because a person testing out a pillow on a mattress who then buys a pillow could have a completely different result when they use their pillow at home, since their mattress may be significantly different from the one they tried at the store. For example, if the user's mattress is firmer than the mattress in the store, the pillow will be too thick, if the user's mattress is softer than the mattress at the store, the pillow will be too low since the pillow sinks into the mattress more. Accordingly, the firmness of a user's mattress is determined by measuring from the photos they submit of how much their bed compresses due to their body weight, this firmness factor is used to adjust and customize the measurements of their pillow, so it keeps their head in alignment with their spine. Furthermore, when a pillow is purchased online, the purchaser has no idea whether the pillow will adequately support their neck in either the back or side sleeper position, or whether the pillow will be adequately sized based on the firmness of their bed.

Figure 6A:
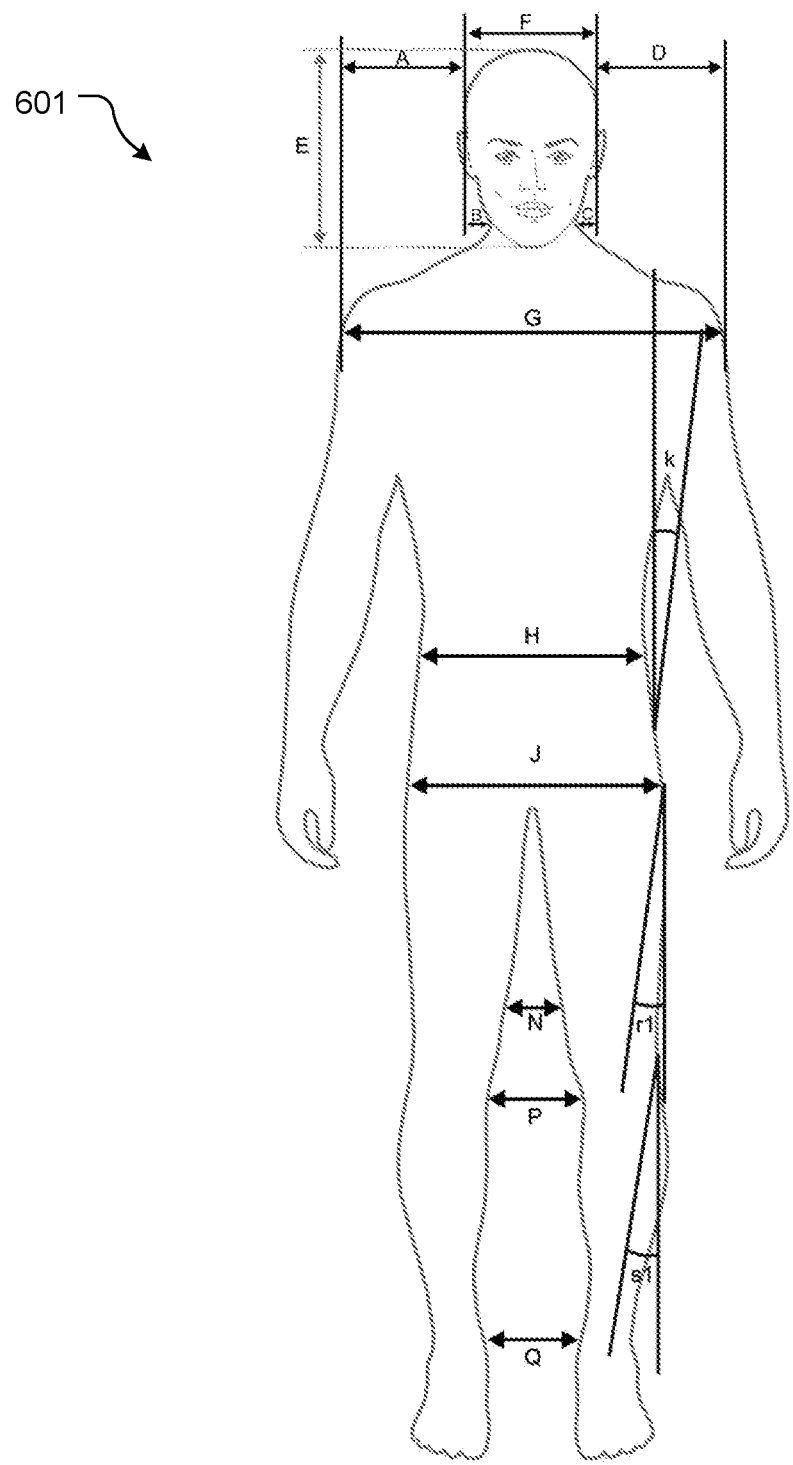
FIGS. 6A and 6B are front diagrams of measurement collection from photos achieved via the system of FIG. 2.
Figure 6B:
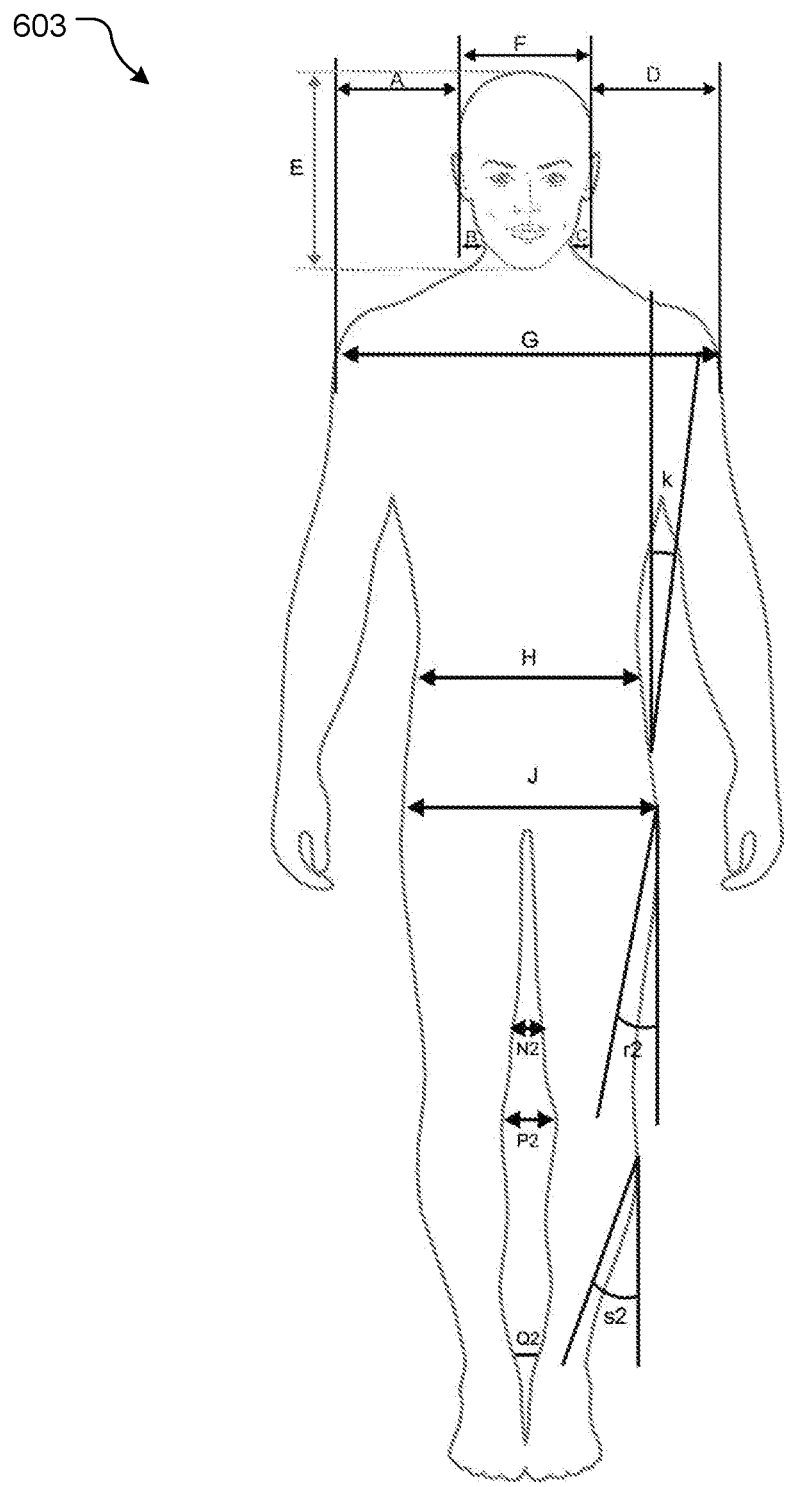

In FIGS. 6A and 6B, diagrams of subject user front facing photos 601, 603 are shown with the user's legs apart and together respectively. The system is configured to determine one or more measurements, including a distance (A) from outside of the subject user's left shoulder to a first edge of the subject user's head; a distance (D) from outside of the subject user's right shoulder to a second edge of the subject user's head; a distance (B) from outside of a left part of the subject user's head to a left side of the subject user's neck; a distance (C) from outside of a right part of the subject user's head to a right side of the subject user's neck; a distance from a top of the user's head to the bottom of their chin (E); a width (G) of the subject user's shoulders; a width (H) of the subject user's waist; a width (J) of the subject user's hips; a height 517 from the user's chin to a top of their head; and a width (F) from a first side to a second side of the user's head.

Additional measurements taken can include: a distance between the user's thighs (N); a distance between the user's knees (P); and a distance between the user's ankles (Q) when the user is standing with their legs apart. These measurements are further compared with a distance between the user's thighs (N2); a distance between the user's knees (P2); and a distance between the user's ankles (Q2) when the user is standing with their legs together.

The plurality of measurements is compared within the computing device and software to determine needed angles associated with the user's body, these angles shown as (K), (r1), (s1), (r2), and (s2) in the diagrams. This provides needed data for the system to calculate the needed pillow details.

Figure 7:
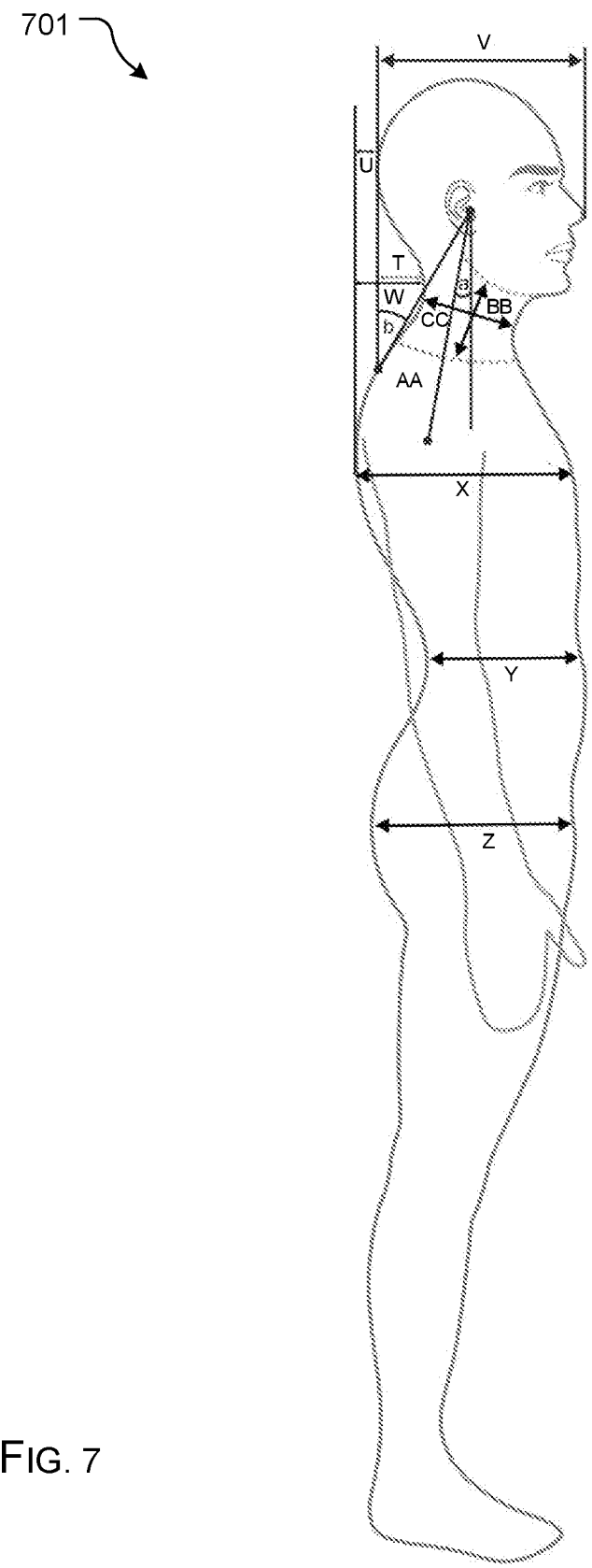
FIG. 7 is a side diagram of measurement collection from photos achieved via the system of FIG. 2.

In FIG. 7, a diagram 701 of a subject user from a side perspective is shown. The system is configured to determine one or more measurements, including a distance (T) from a back of the subject user's neck to a back of the subject user's head; and a distance (U) from a back of the subject user's head to a back of the subject user's back; a length (V) from a front to back of the user's head; a distance from a back of the subject user's neck to the user's back (W); a chest depth from a front of the user's chest to the user's back (X); a depth of the user's waist (Y); and a depth of the user's hips (Z).

Additional measurements can include: a distance from the user's ear to their shoulder (AA); a distance from the user's jaw to the base of their neck (BB); and a distance from a front to back of the user's neck (CC). Again, it should be appreciated that the measurements are used to calculate angles (a); (b) to determine the subject user's shape, and therefore calculate the best pillow features.

Figure 8:
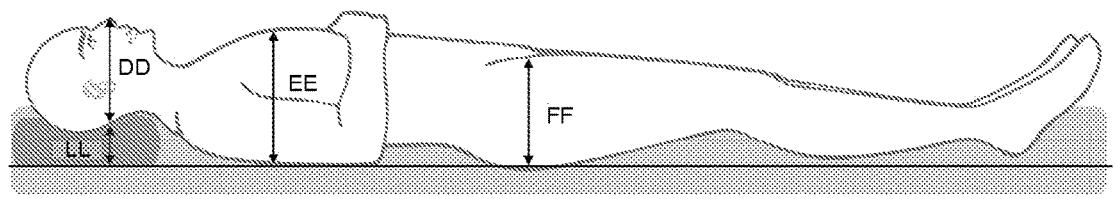
FIG. 8 is a side diagram of measurement collection from lying down photos achieved via the system of FIG. 2.
Figure 9:
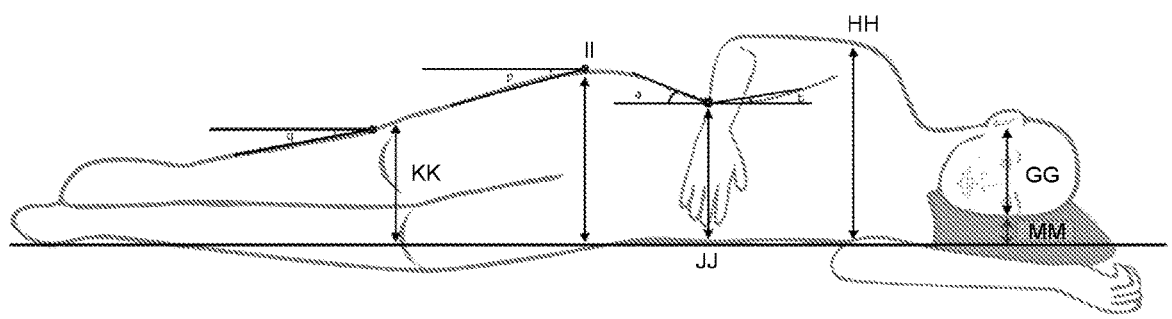
FIG. 9 is a front diagram of measurement collection from lying down photos achieved via the system of FIG. 2.

In FIGS. 8 and 9, diagrams 801, 901 depicts lying down diagrams of the subject user photos, wherein even more measurements are calculated. These measurements to include: a distance from a front of the user's head to the back of the user's head (DD); a distance from the front of the user's chest to their back (EE); a distance from a front to back of the user's hips (FF); a distance from a side to side of the user's head (GG); a distance from a top of the user's upward shoulder to the bed (HH); a distance from a top of the user's hips to the bed (II); a distance from a top of the user's waist to the bed (JJ); and a distance from the top of the user's knees to the bed (KK). It should be appreciated that additional calculations, including a pillow thickness from the side when the user is lying on their back (LL) and also when the user is lying on their side (MM), can be taken.

Again, these measurements and photos are used to calculate angles (a), (b), (p), (q) associated with the user's body.

By measuring the size of the neck and the location of the neck relative to their back when laying on their back and to their shoulder when sleeping on their side, the correct neck support can be provided so the head and neck are in alignment with the spine. This helps sleepers go to sleep faster, suffer less discomfort and feel more rested without the classic crook in their neck. These measurements determine the size of the neck support and account for the compressibility of the pillow, the compressibility of the mattress, the weight of the individual and the distribution of their weight on their neck and their head.

Figure 10:
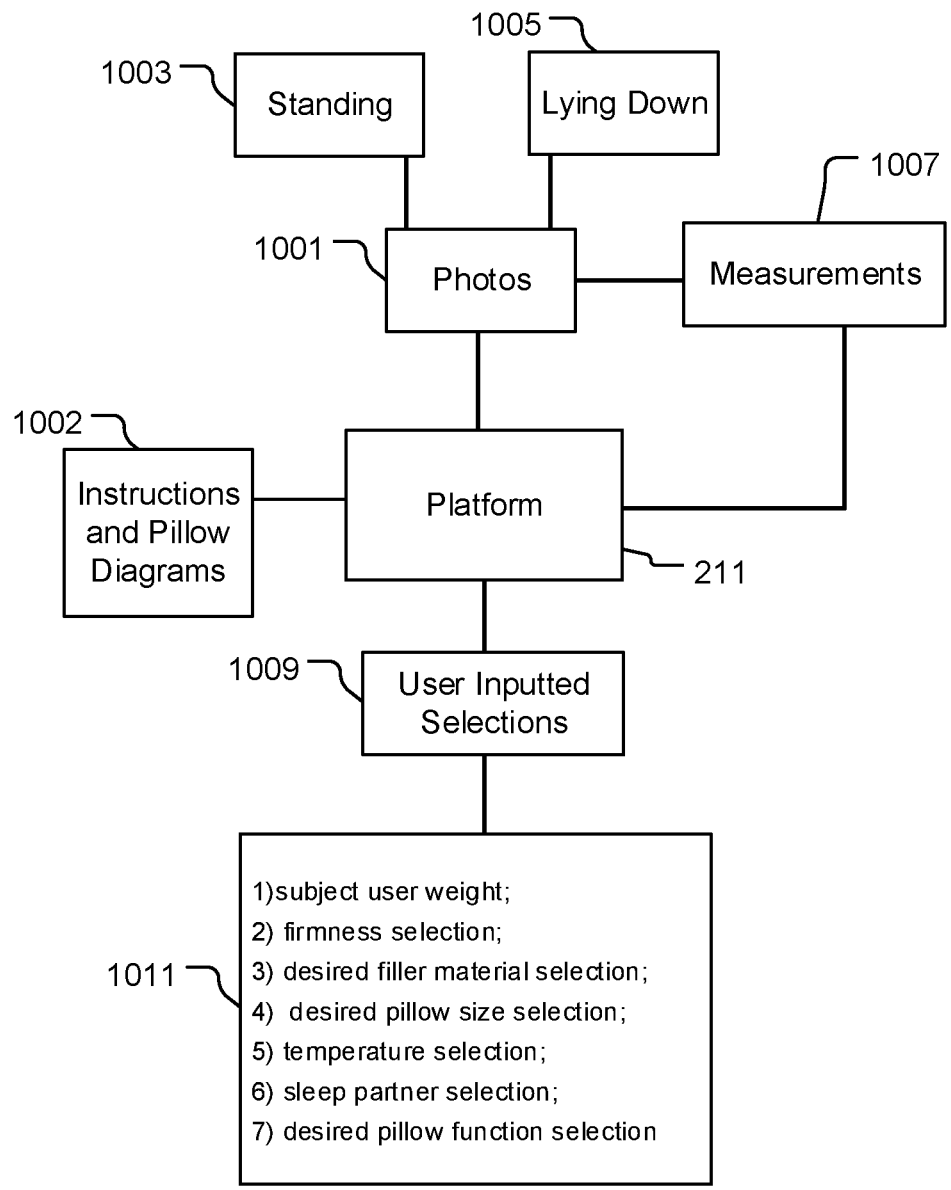
FIG. 10 is a simplified schematic of the features of a platform of FIG. 2.

In FIG. 10, a simplified schematic depicts the user platform 211 configured to receive the photos and user inputted selections based on instructions and pillow diagrams 1002. The platform 1011 is configured to take and transfer photos 1001. The photos are to include both standing positions 1003 of the subject user, as well as lying down positions 1005 of the subject user. The lying down photos show the user on their mattress, thereby providing data to determine mattress firmness, as described above. From the photos, the server is configured to analyze, using one or more algorithms, to determine subject user measurements 1007.

The instructions provided to the user can include instructing the user to hold a device, such as a credit card in order to provide a reference size, instructions on what to wear, what colors to wear, what pictures to take, long hair directions, and facial hair directions. The platform can further provide instructions for the lying down photo capturing, including providing direction on camera angle, camera distance, sheet color, and wall colors.

Platform 211 is further configured to receive subject user selections 1009, the selections including one or more 1011 of: (1) subject user weight; (2) firmness selection associated with one or more zones of a pillow diagram; (3) desired filler material selection, such as hypoallergenic or breathable; (4) desired pillow size and shape selection; (5) temperature selection, wherein the user selects from one of cooling, warming, and neutral; (6) sleep partner selection, such as whether the subject user sleeps with a partner and/or a pet; and (7) desired pillow function selection, such as whether the pillow is to be used as a head pillow, back pillow, front pillow, between the legs pillow, or travel pillow. It is contemplated that any number of other selections could be provided, such as the option for a cover and the material of the cover, the options including color, pattern type of material, sweat retardant solutions, quality of material, thread count, bamboo, or any other material.

It is contemplated that possible materials for use, can include foam, memory foam, cubes of foam, polyester fibers, goose down, cotton, latex, hypoallergenic, features, buckwheat husks, or any other material.

Figure 11:
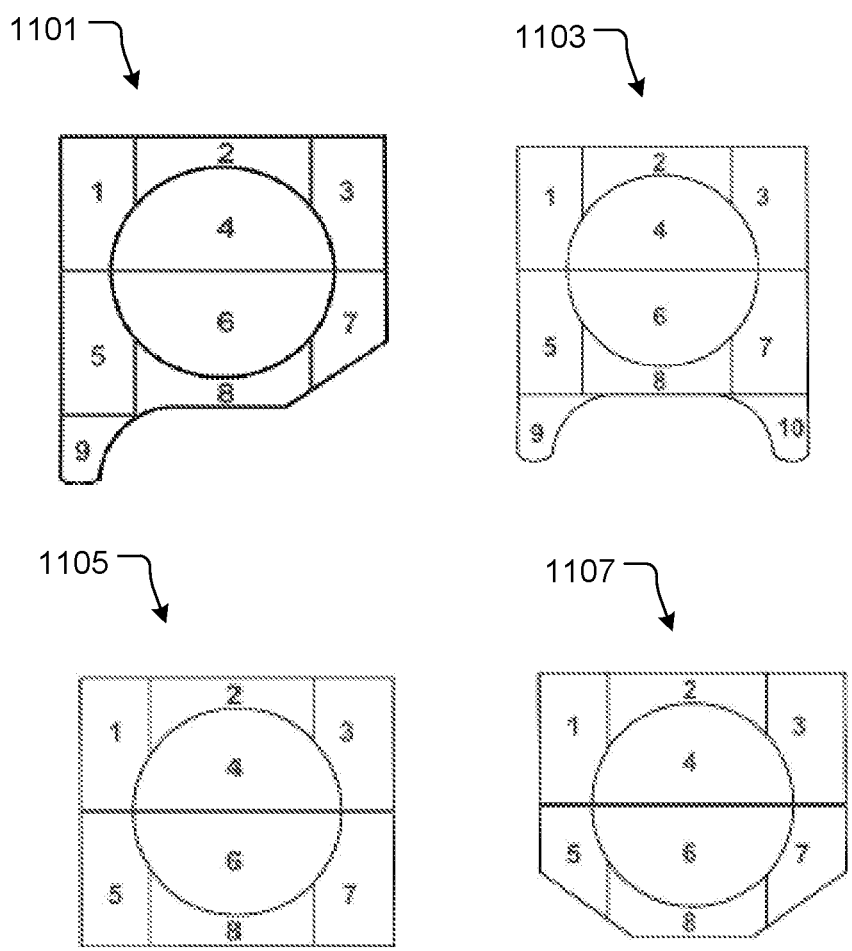
FIG. 11 is a plurality of diagrams of pillow shapes and zones contemplated for use with the system of FIG. 2.

In FIG. 11, a plurality of pillow diagrams 1101, 1103, 1105, 1107 are shown, wherein each diagram has a specified shape and includes a plurality of zones. Through the platform, the user can make selections of what zones they want firm or soft, as well as select a desired shape. It is contemplated that any number of shapes and/or zones could be used herein. It is contemplated that each zone can have its own access via zipper, snaps, hook and loop fasteners, or other connection solution. This will allow someone to adjust the pillow to their own liking if the pillow changes shape or the filling loses some of its shape over time.

Figure 12A:
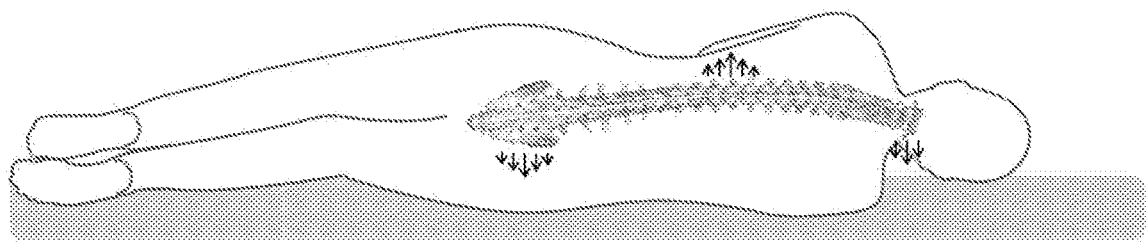
FIGS. 12A and 12B are back diagram views depicting proper spine alignment achieved via pillow customization.
Figure 12B:
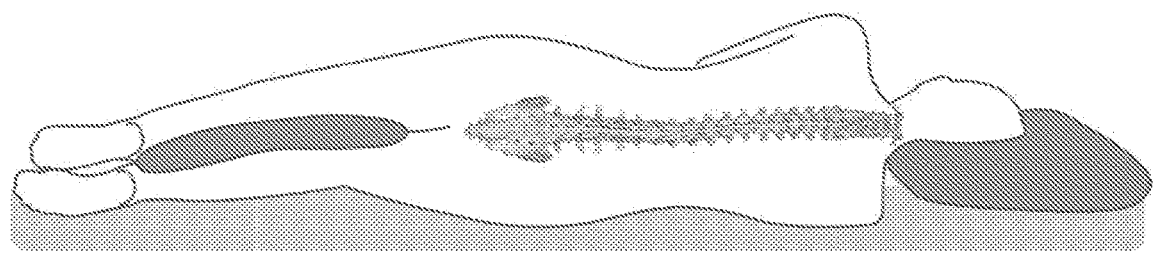

In FIGS. 12A and 12B, back views depict diagrams 1201, 1203 that show proper alignment of the user's spine as achieved when the user is provided with two customized pillows (a head and leg pillow) to correct spine alignment.

Figure 13A:
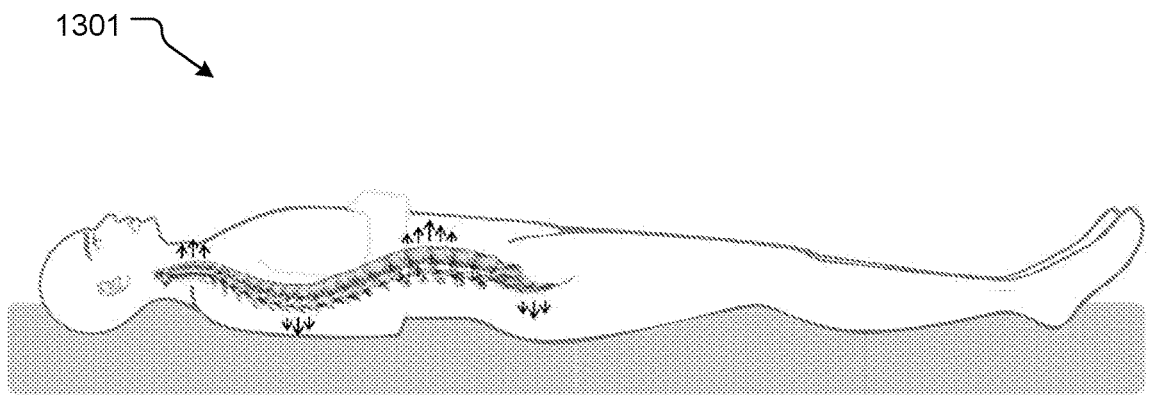
FIGS. 13A and 13B are side diagram views depicting proper spine alignment achieved via pillow customization.
Figure 13B:
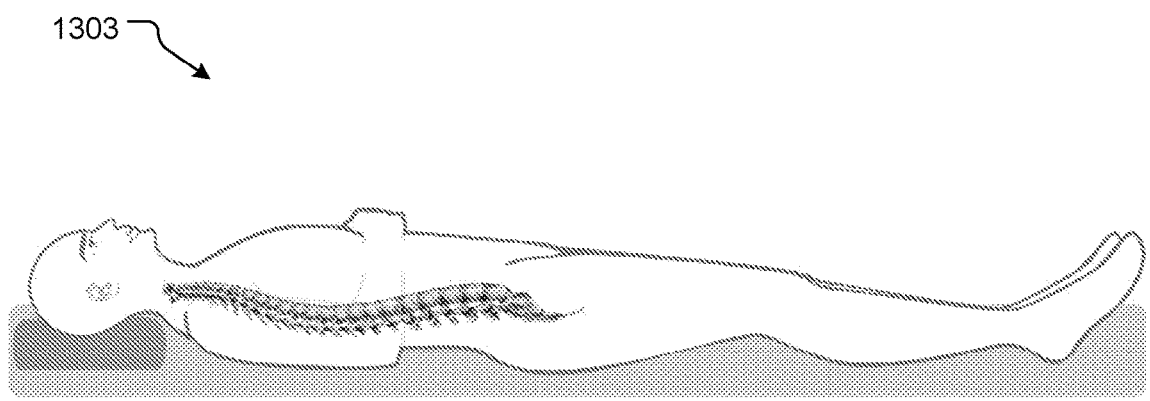

In FIGS. 13A and 13B, side views depict diagrams 1301, 1303 that show proper alignment of the user's spine as achieved when the user is provided with a customized pillow.

Figure 14:
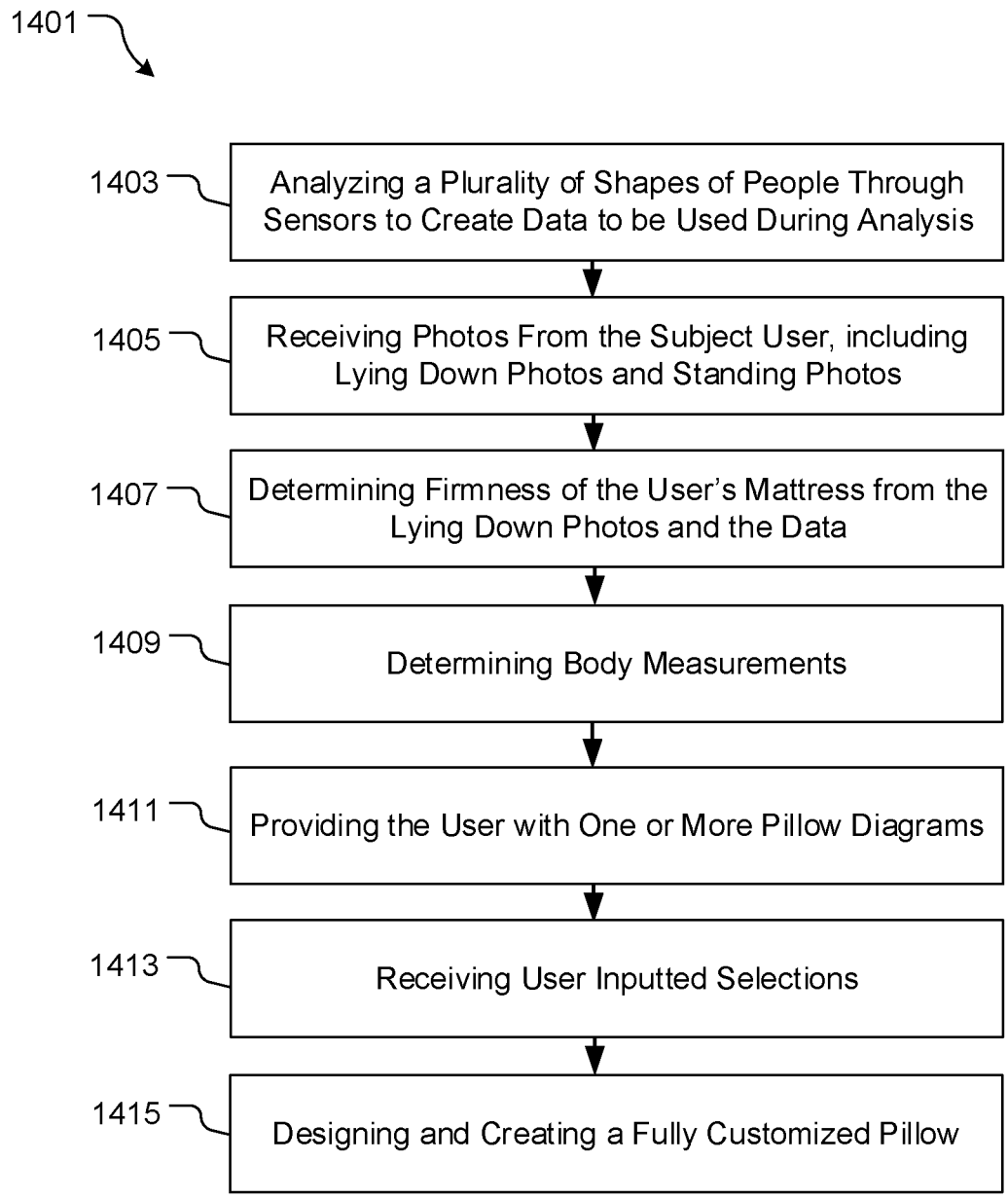
FIG. 14 is a flowchart of a method of use of the system of FIG. 2.

In FIG. 14, a flowchart 1401 depicts a method associated with system 201. During use, the system analyzes the plurality of shapes of people to create data for use, as shown with box 1403. When a person desires to create a customized pillow, the subject user uses the platform to provide photos, as shown with box 1405. The system then processes data, with one or more algorithms, to determine a mattress firmness, and body measurements, as shown with boxes 1407, 1409. The user is then provided with one or more pillow diagrams, wherein the user can provide user inputted selections, as shown with boxes 1411, 1413. Based on all data received, a customized pillow is designed, manufactured, and provided to the subject user, as shown with box 1415.

Figure 15:
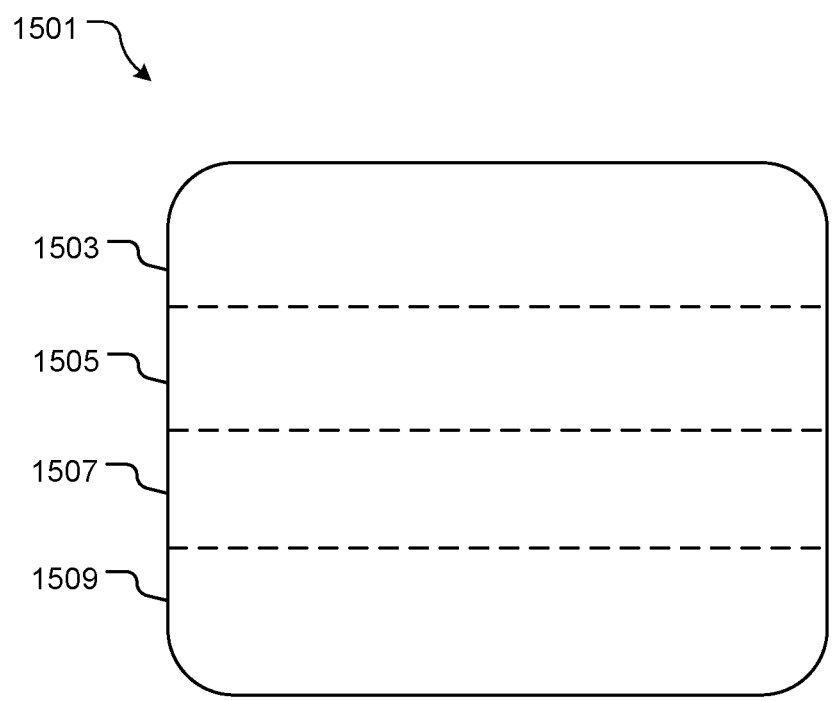
FIG. 15 is a top view of an alternative embodiment of a pillow in accordance with the present application.
Figure 16:
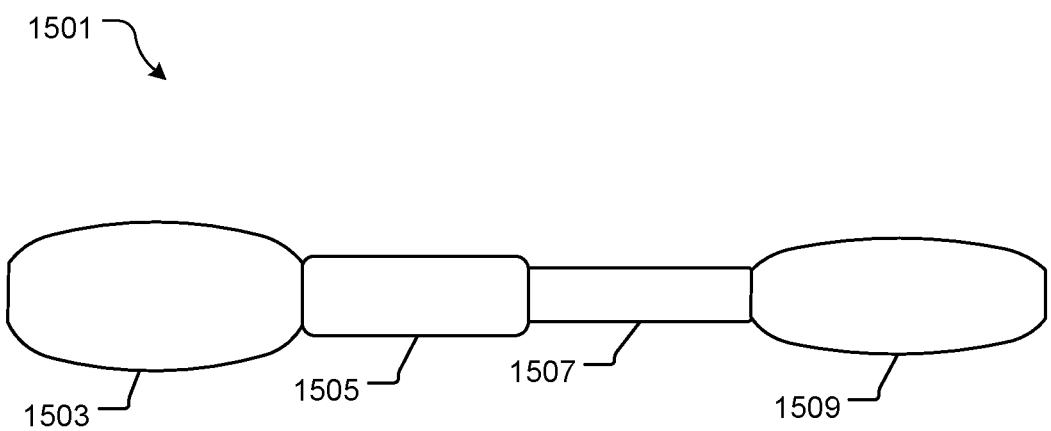
FIG. 16. is a side view of the pillow of FIG. 15.

In FIGS. 15 and 16, top and side views of a pillow 1501 as developed via the system of the present invention is shown. In this embodiment, the pillow 1501 has four sections, wherein the sections provide for alternative sleeping positions for the user. In this embodiment, section 1503 is to be used for a side sleeper neck rest, section 1505 is to be used for a side sleeper head rest, section 1507 is to be used for a back sleeper head rest, and section 1509 is to be used for a back sleeper neck rest. It should be appreciated that during use, the user merely rotates the pillow 180 degrees to switch between back and side sleeping. As shown in FIG. 16, the pillow has different fill levels based on the sleeping position intended for use. The sections are integrally secured together, and the pillow can be configured to open on one or more sides to allow for filling of the sections.

Figure 17:
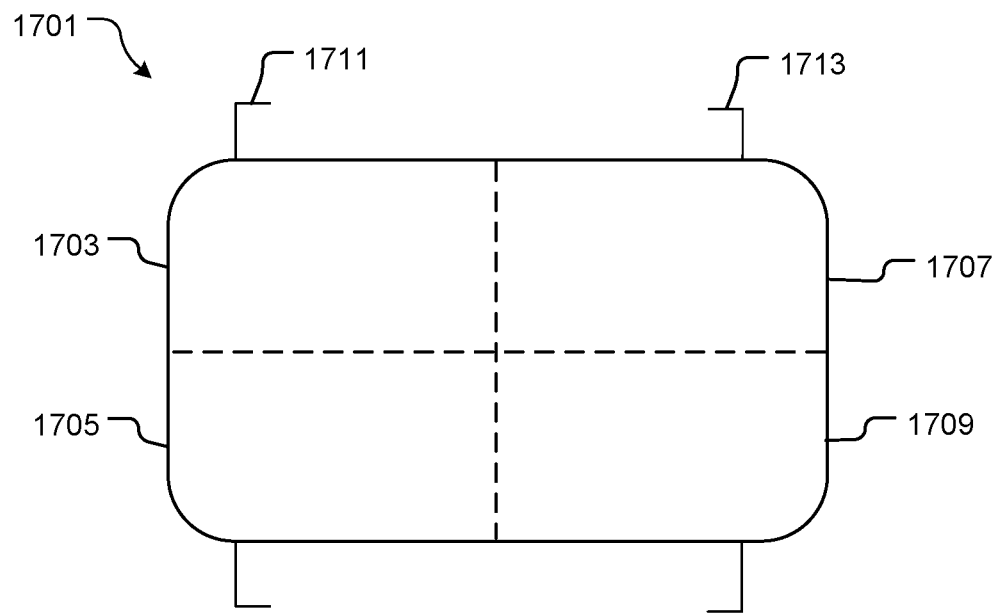
FIG. 17 is a top view of an alternative embodiment of a pillow in accordance with the present application.
Figure 18A:
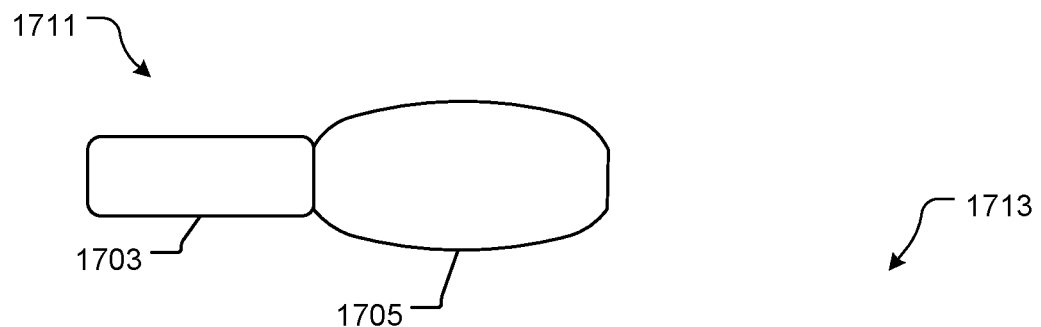
FIGS. 18A and 18B are end cross sectional views of the pillow of FIG. 17.
Figure 18B:
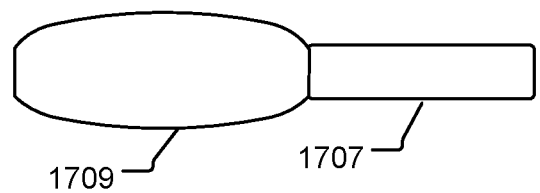

In FIGS. 17 and 18, another alternative pillow 1701 is shown having a plurality of sections, wherein the sections provide for alternative sleeping positions by the user. FIG. 18A is an end view of pillow 1701 showing cross section 1711. FIG. 18B is an opposite end view of pillow 1701 showing cross section 1713. In this embodiment, section 1703 is to be used for a side sleeper head rest, section 1705 is to be used as a side sleeper neck rest, section 1707 is to be used as a back sleeper head rest, and section 1709 is to be used as a back sleeper neck rest. This configuration allows for the user to merely move to the side and use a different half of the pillow based on their desired sleeping position.

The system of the present invention provides for pillow customization, which provides for a plurality of benefits. The pillow can further be customized, wherein the pillow is appropriate for sleeping in multiple positions, wherein the user can orient the pillow at different angles to fit their particular need.

Figure 19:
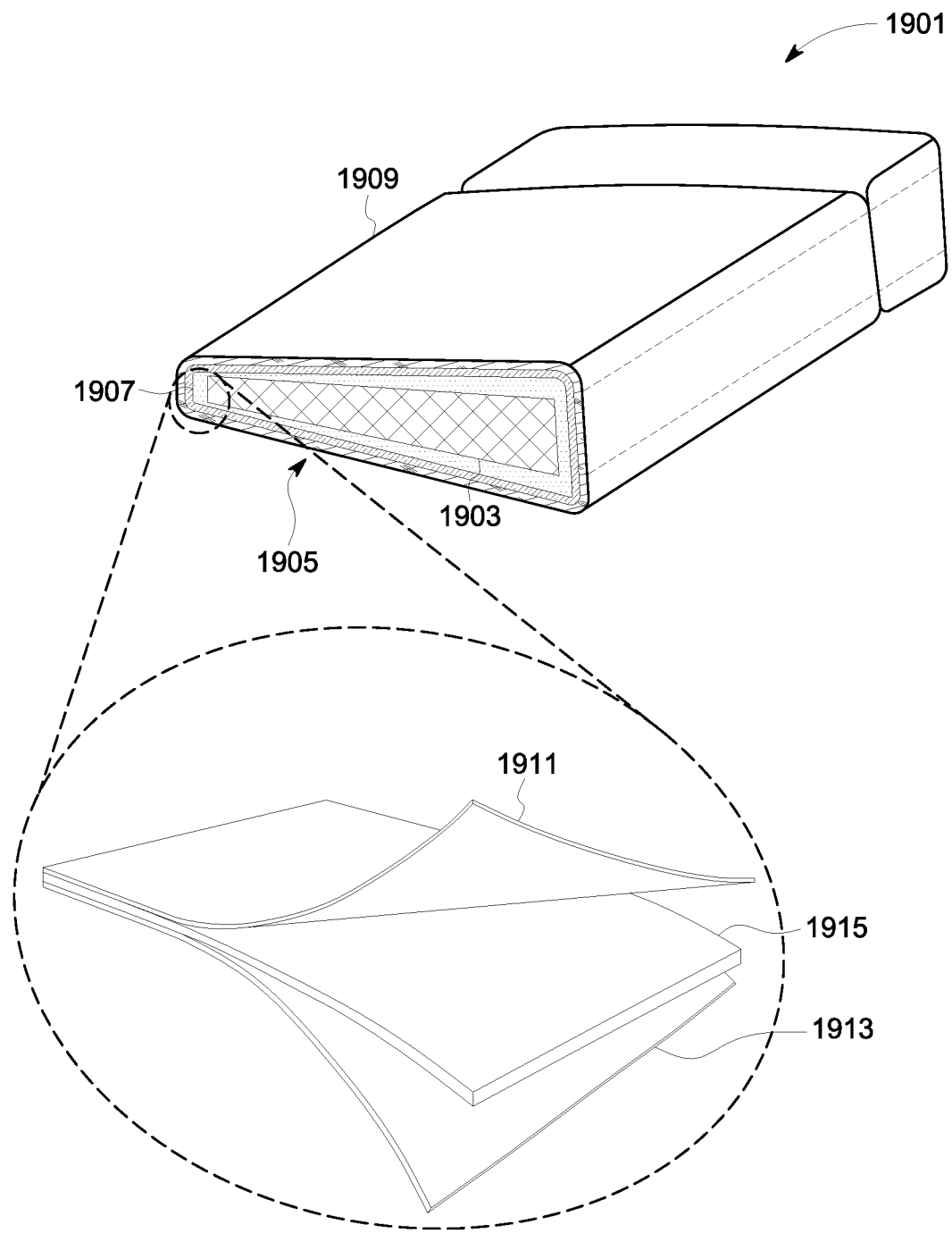
FIG. 19 is an isometric view of an embodiment of a pillow as created by the method of the present invention.
Figure 20:
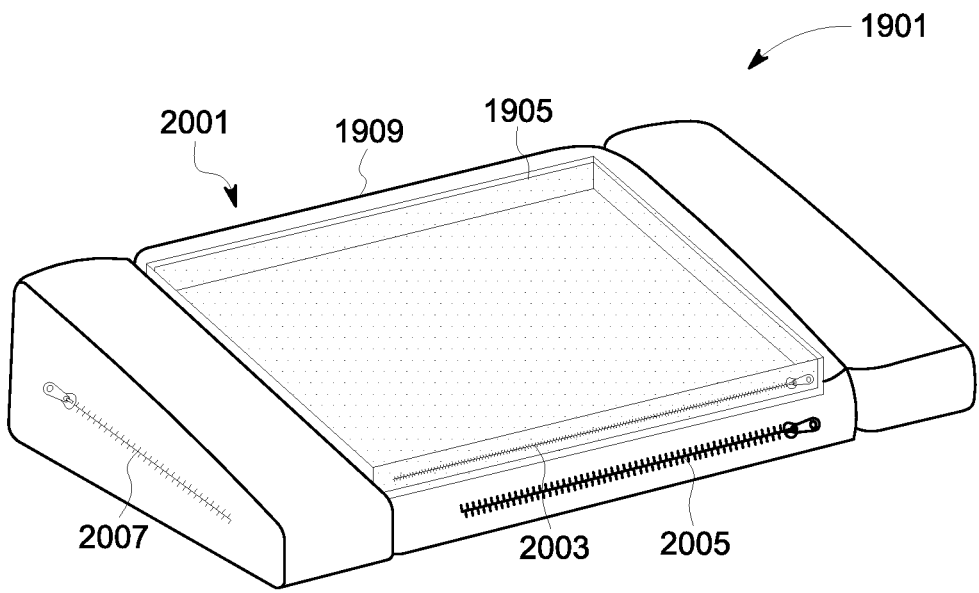
FIG. 20 is a front isometric view of the embodiment of the pillow of FIG. 19.
Figure 21:
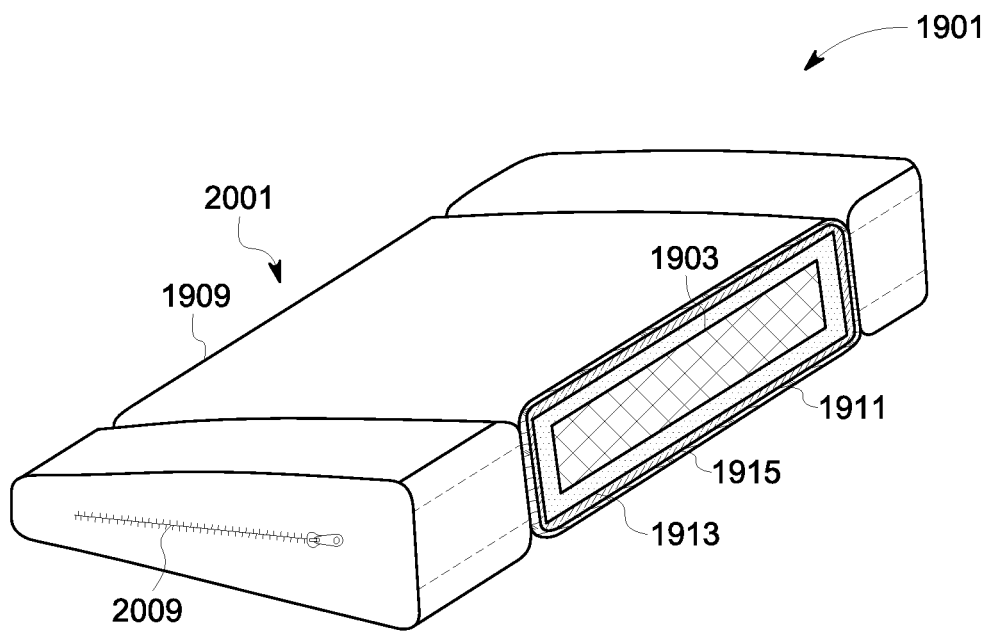
FIG. 21 is a back isometric view of the embodiment of a pillow of FIG. 29.

In FIGS. 19-21, a pillow 1901 as created by the present invention is shown. In this embodiment, pillow 1901 is particularly suitable for side sleepers. As shown, pillow 1901 includes a foam interior core 1903 that is tapered from a first side 1905 to a second side 1907. In some embodiments, the foam core is surrounded by a cover 1909, the cover having an exterior satin layer 1911; an interior Egyptian cotton layer 1913; and a middle polyester layer 1915 positioned between the exterior satin layer and interior Egyptian cotton layer.

As best shown in FIGS. 20 and 21, the foam core 1903 can be removably inserted within a center portion 2001 of the pillow body. It is contemplated that the opening into the center portion 2001 can be secured via a zipper 2003 or other suitable means. In addition, the opening can provide access to a plurality of pockets, such as being configured to receive the foam core and polyester fiber. Further, as shown, there can be additional openings 2005, 2007, 2009 for the user to remove and add fiber as desired.

It should be appreciated that the pillow 1901 provides for benefits over the prior art. Namely, the foam core aids in keeping the user cool while sleeping, which provides for an improved sleeping experience. The foam core further provides for proper firmness and a flatter profile for side sleepers, thereby properly supporting the user's head and reducing downward and lateral deformation of the pillow as someone sleeps thereon. The ability to remove the foam insert, and other fiber materials, allows for the cover to be washable. Yet further, the tapering of the foam insert allows for the user's head to compress the thickest portion of the foam insert such that their head will be positioned in a substantially flat position.

In FIGS. 22-28, views of pillows associated with a set of pillows as created using the system of the present invention are shown. It is contemplated that the system can be used to create a set of pillows that is particularly suitable for a side sleeper. This set of pillows will include a head pillow 2401, a huggable pillow 2201; a knee to ankle leg support pillow 2501; and a hand support pillow 2701. In this embodiment, the head pillow 2401 is created as already discussed above.

Figure 22:
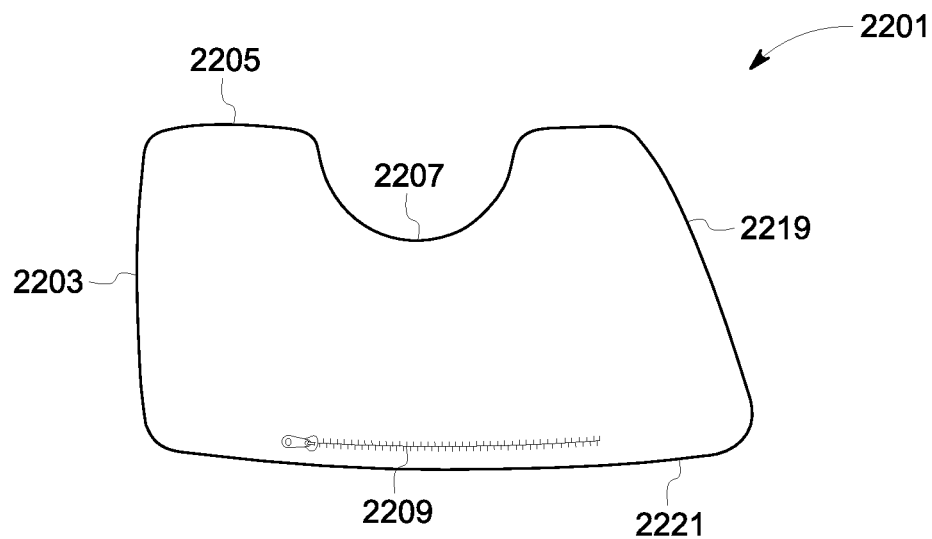
FIG. 22 is a front view of a huggable pillow as created by the method of the present invention.
Figure 23:
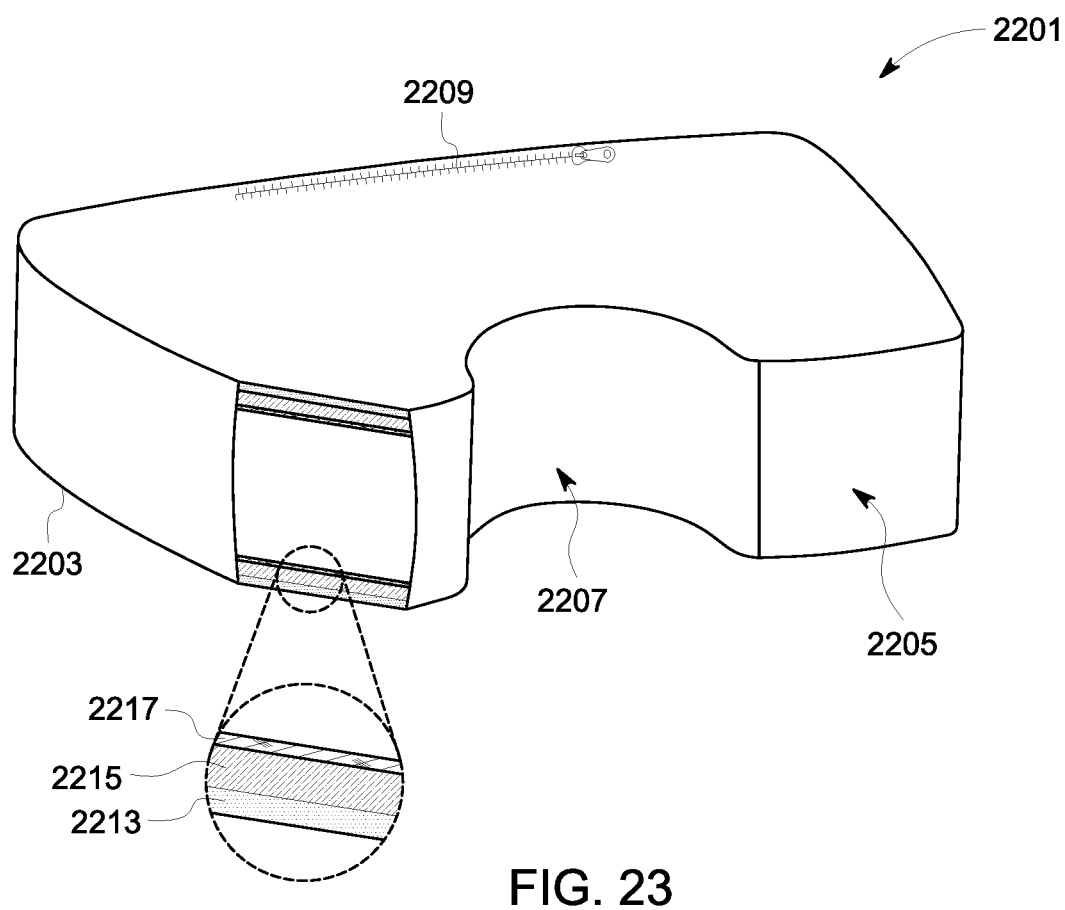
FIG. 23 is an isometric view of the huggable pillow of FIG. 22 with a cutout for clarity.
Figure 24:
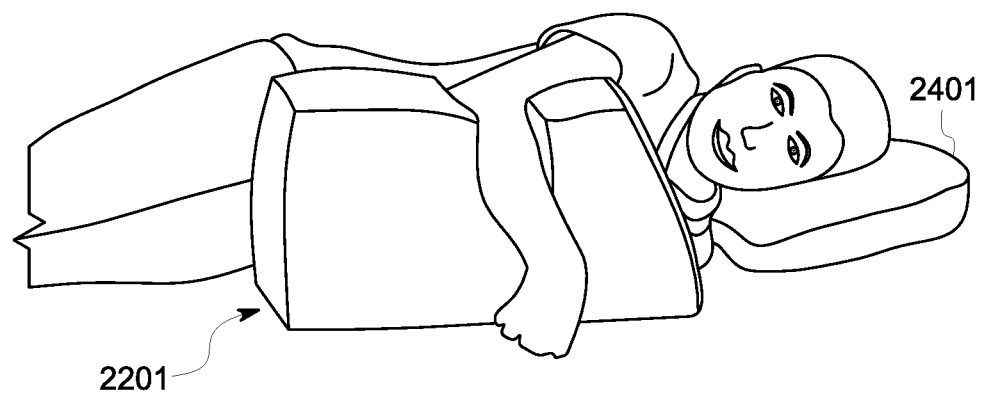
FIG. 24 is a front view of a side sleeping position in accordance with the present invention.

In FIGS. 22-24, the huggable pillow 2201 is shown. This pillow 2201 including a body 2203 that includes a top edge 2205, the top edge 2205 having a concave cutout 2207 extending into the body of the pillow. This concave cutout 2207 provides for a location for the user to place their arm in a side sleeping position, as shown in FIG. 24. In addition, the huggable pillow 2201 can include an opening 2209, wherein the interior filler is removable from a cover 2211, the cover having a satin 2213, polyester 2215, and Egyptian cotton 2217 layers. As further shown, in some embodiments, the body further includes one or more tapered sides 2219 extending from the top edge to a bottom edge 2221, thereby being configured to prevent slipping and movement of the pillow during use. It should further be appreciated and understood that the huggable pillow is customizable in width, height, length, depth of cutout, and filler material as previously described.

Figure 25:
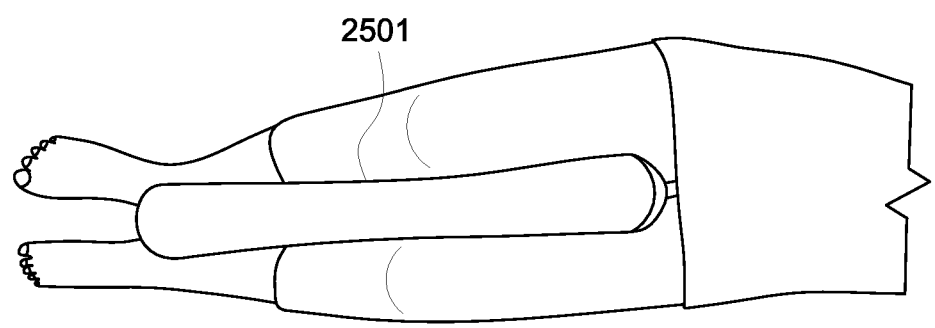
FIG. 25 is a front view of the side sleeping position in accordance with the present invention.
Figure 26:
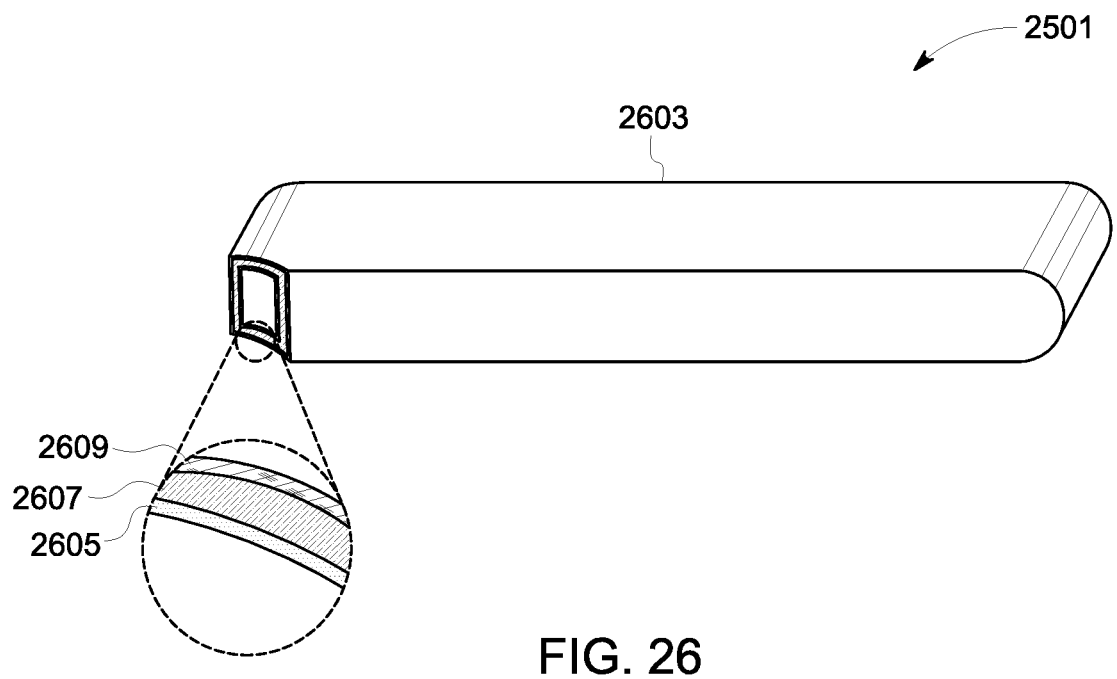
FIG. 26 is a front view of a knee to ankle support pillow as created by the method of the present invention.

In FIGS. 25 and 26, an embodiment of the knee to ankle leg pillow 2501 for use in a side sleeping position is shown. As shown, the pillow includes the cover 2603 with the layers discussed above, namely a satin 2605, polyester 2607, and Egyptian cotton layer 2609. It should be appreciated that the pillow 2501 is customizable in length, thickness, filler, shape, taper, firmness, and other factors based on the user's unique measurements as described above.

Figure 27:
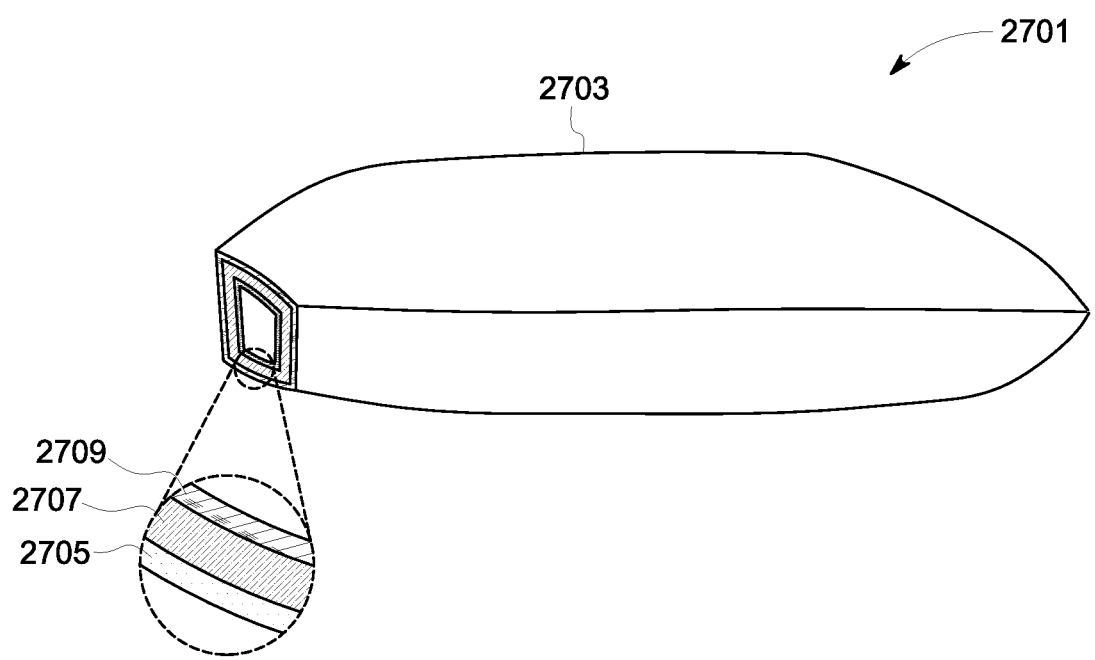
FIG. 27 is a front view of a hand support pillow as created by the method of the present invention.
Figure 28:
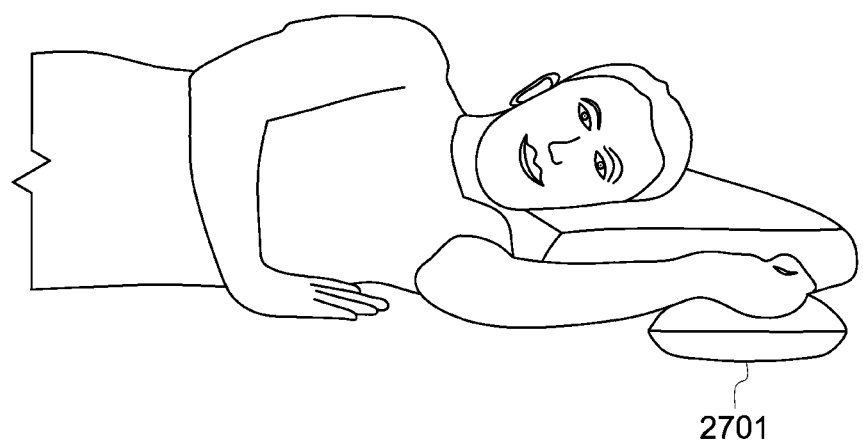
FIG. 28 is a front view showing use of the hand support pillow of FIG. 27.

In FIGS. 27 and 28, a hand support pillow 2701 is shown. The hand support pillow being customizable in height, width, firmness, filler, morphology, and other parameters as discussed above, thereby being properly suited for a user. It should be appreciated that the hand support pillow supports the user's lower arm, thereby preventing discomfort generally caused to this arm during side sleeping. As shown, the pillow 2701 can also include a cover 2703 with the layers previously discussed, namely a satin 2705, polyester 2707, and Egyptian cotton 2709 layer.

It should be appreciated and understood that the use of the set of pillows will help the user achieve a high level of comfort by providing support to various areas of the body to align the user's body as needed for rest and sleep. The ability to customize each pillow further aids in allowing a user to find an optimal set of pillows that works best for them.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. A method of pillow customization, the method comprising:
   analyzing a plurality of shapes associated with people through the use of a plurality of sensors to create a database of analytical data;
   receiving a plurality of photos from a subject user through a first computing device and a server;
   determining a firmness of a mattress of the subject user based on the plurality of photos and the analytical data;
   determining a plurality of body measurements of the subject based on the plurality of photos through one or more algorithms and a second computing device;
   providing the subject user with a pillow diagram, the pillow diagram having one or more zones, each of the one or more zones being customizable in firmness;
   receiving one or more subject user inputted selections through the first computing device; and
   designing a pillow based on the firmness of the mattress, the plurality of body measurements, and the one or more subject user inputted selections, the pillow being customized to the subject user.

2. The method of claim 1, wherein the pillow further comprises:
   a body having a center portion;
   an opening into the center portion; and
   a foam core removably secured within the center portion.

3. The method of claim 2, wherein the pillow further comprises:
   a cover surrounding the body, the cover having:
      an exterior satin layer;
      an interior Egyptian cotton layer; and
      a middle polyester layer positioned between the exterior satin layer and interior Egyptian cotton layer.

4. The method of claim 3, wherein the cover surrounds the foam core.

5. The method of claim 2, wherein the opening is closed via a zipper.

6. The method of claim 2, wherein the foam core is tapered from a first side to a second side.

7. A method of pillow customization, the method comprising:
   analyzing a plurality of shapes associated with people through the use of a plurality of sensors to create a database of analytical data;
   receiving a plurality of photos from a subject user through a first computing device and a server;
   determining a firmness of a mattress of the subject user based on the plurality of photos and the analytical data;
   determining a plurality of body measurements of the subject based on the plurality of photos through one or more algorithms and a second computing device;
   providing the subject user with a pillow diagram, the pillow diagram having one or more zones, each of the one or more zones being customizable in firmness;
   receiving one or more subject user inputted selections through the first computing device;
   determining that the user is a side sleeper; and
   designing a set of pillows based on the firmness of the mattress, the plurality of body measurements, and the one or more subject user inputted selections, the set pillow being customized to the subject user and being suitable for a side sleeping position.

8. The method of claim 7, wherein the set of pillows comprises:
   a head pillow;
   a huggable pillow;
   a knee to ankle leg support pillow; and
   a hand support pillow.

9. The method of claim 8, wherein the huggable pillow comprises:
   a body having a top edge with a concave cut out extending into the body from the top edge, the concave cut out configured to receive a user's arm when sleeping.

10. The method of claim 9, wherein the huggable pillow further comprises:
    a cover, having:
       an exterior satin layer;
       an interior Egyptian cotton layer; and
       a middle polyester layer positioned between the exterior satin layer and interior Egyptian cotton layer.

11. The method of claim 9, wherein the body further comprises:
    a side edge tapering from the top edge to a bottom edge, wherein the tapering is configured to prevent sliding.

* * * * *